United States Patent [19]

Szántay et al.

[11] Patent Number: 4,806,545

[45] Date of Patent: Feb. 21, 1989

[54] (−)-1β-ETHYL-1α-HYDROXYMETHYL-1,2,3,4,6,7,12,12Bα-OCTAHYDROINDOLO(2,3-A)QUINOLIZINE, PROCESS FOR ITS PREPARATION AND PHARMACEUTICAL COMPOSITIONS CONTAINING SAME

[75] Inventors: Csaba Szántay, Budapest; Lajos Szabó, Budapest; György Kalaus, Budapest; Zsolt Szombathelyi, Budapest; Egon Kárpáti, Budapest; Béla Kiss, Vecses; Katalin Csomor, Budapest; István Laszlovszky, Budapest; Erzsébet Lapis, Budapest; László Szporny, Budapest; Lilla Forgács, Budapest; Csaba Kuthi, Budapest; Anikó Gere, Budapest, all of, Hungary

[73] Assignee: Richter Gedeon Vegyeszeti Gyar Rt., Budapest, Hungary

[21] Appl. No.: 851,327

[22] Filed: Apr. 14, 1986

[30] Foreign Application Priority Data

Apr. 19, 1985 [HU] Hungary .............................. 1519/85

[51] Int. Cl.[4] ............................................ C07D 455/00
[52] U.S. Cl. ........................................ 514/285; 546/70
[58] Field of Search ........................... 546/70; 514/285

[56] References Cited

U.S. PATENT DOCUMENTS 4,036,841  7/1977  Szantay et al. ......................... 546/70

OTHER PUBLICATIONS

Helv. Chem. Acta., 60, 1801–1810 (1977).
Gaz. Chem. Italiana, 111, 257–267 (1981).

Primary Examiner—Donald G. Daus
Assistant Examiner—C. L. Cseh
Attorney, Agent, or Firm—Herbert Dubno; Jonathan Myers

[57] ABSTRACT

The invention relates to the new (−)-1β-ethyl-1α-hydroxymethyl-1,2, 3,4,6,7,12,12ba-octa-hydroindolo[2,3-a] quinolizine of the formula (I)

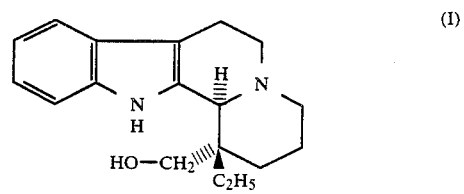

and acid addition salts thereof.

According to another aspect of the invention there is provided a process for the preparation of the compound of formula (I) and acid addition salts thereof by resolution of the corresponding racemic compound and optionally by subsequent hydrolysis and/or salt formation.

The compound of formula (I) shows a remarkable peripheral vasodilating and antihypoxial activity. Pharmaceutical compositions comprising it as active ingredient are also within the scope of the invention.

7 Claims, No Drawings

(−)-1β-ETHYL-1α-HYDROXYMETHYL-1,2,3,4,6,7,12,12Bα-OCTAHYDROINDOLO(2,3-A)QUINOLIZINE, PROCESS FOR ITS PREPARATION AND PHARMACEUTICAL COMPOSITIONS CONTAINING SAME

The invention relates to a new, optically active 1-ethyl-octahydroindolo[2,3-a]quinolizine derivative containing the 1-ethyl group and the 12b-hydrogen in trans configuration. More particularly, the invention concerns the new, optically active, trans (−)-1β-ethyl-1α-hydroxymethyl-1,2,3,4,6,7,12,12bα-octahydroindolo[2,3-a]quinolizine of the formula (I)

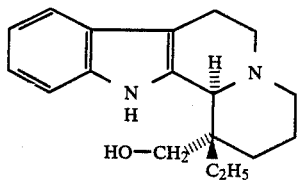

(I)

and acid addition salts thereof.

According to another aspect of the invention there is provided a process for the preparation of the compound of formula (I) and acid addition salts thereof, which process comprises subjecting a 1:1 mixture of a 1α-ethyl-1β-acyloxymethyl-1,2,3,4,6,7,12,12bβ-octahydroindolo[2,3-a]quinolizine derivative of the formula (IIa)

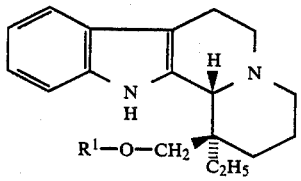

(IIa)

and a 1β-ethyl-1-α-acyloxymethyl-1,2,3,4,6,7,12,12bα-octahydroindolo[2,3-a]quinolizine derivative of the formula (IIb)

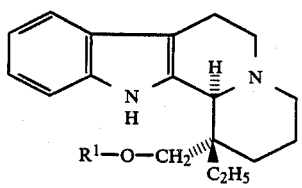

(IIb)

wherein $R^1$ is hydrogen, alkylcarbonyl having from 1 to 6 carbon atoms in the alkyl moiety, optionally substituted arylcarbonyl or aralkylcarbonyl having from 1 to 6 carbon atoms in the alkyl moiety,
to resolution, and optionally subjecting a new optically active (−)-1β-ethyl-1α-acyloxymethyl-1,2,3,4,6,7,12,12bα-octahydroindolo[2,3-a]quinolizine derivative of the formula (III)

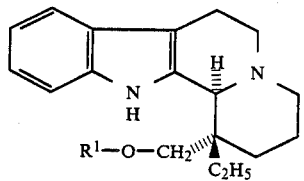

(III)

wherein $R^2$ is alkylcarbonyl having from 1 to 6 carbon atoms in the alkyl moiety, optionally substituted aryl or aralkylcarbonyl having from 1 to 6 carbon atoms in the alkyl moiety,
obtained to hydrolysis, and, if desired, treating the obtained new (−)-1β-ethyl-1α-hydroxymethyl-1,2,3,4,6,7,12,12bα-octahydroindolo[2,3-a]quinolizine of the formula (I) with an acid.

In the above formulae $R^1$ and $R^2$ as an alkyl group may represent any straight-chained or branched alkyl having from 1 to 6 carbon atoms, e.g. a methyl, ethyl, n-propyl, isopropyl, n-butyl, isobutyl, tert.-butyl, n-pentyl, isopentyl, etc. group. As an aryl group $R^1$ and $R^2$ may represent a mono- or polycyclic (separate or fused) aromatic hydrocarbon group, such as e.g. a phenyl, diphenyl or naphthyl group, etc. The term "aralkyl" is used to refer to any combination of the above-identified aryl and alkyl groups.

The compound of the formula (I) shows an excellent pharmaceutical, in particular cardiovascular, especially peripheral vasodilating and antihypoxial activity.

In the Hungarian Patent Specification No. 170,495 (British Patent Specification Nos. 1,499,546, 4036841) there were disclosed 1,1-disubstituted octahydroindolo[2,3-a]quinolizines, which may carry in the 1-position, amongst others, substituents identical with those present in the compound according to the invention. In those compounds, however, the configuration of the substituents in the 1-position and of the 12b-hydrogen was not specified; moreover, although in the specification and claims the optically active compounds and the resolution process are also disclosed in general terms, the specifically disclosed compounds are without exception racemic.

The known racemic compounds possess vasodilating properties, and this activity can be observed both in the peripheral and in the cerebral circulation, i.e. the vasodilating activity of said compounds is not selective. In sharp contrast, the compound according to the invention has a selective peripheral vasodilating activity. A further difference between the earlier, known compounds and the compound according to the invention is that the former ones have no antihypoxial activity, while in the case of the compound according to the invention the peripheral vasodilating activity is accompanied by antihypoxial activity.

According to Helv. Chim. Acta, 60, 1801 (1977) racemic trans 1-ethyl-1-hydroxymethyl-1,2,3,4,6,7,12,12b-octahydroindolo[2,3-a]quinolizine was prepared by reducing a corresponding racemic trans compound containing an aldehyde group in the 1-position obtained as an intermediate in vincamine synthesis. There is, however, no mention in the cited article about the resolution of the compound obtained, about the corresponding optically active compounds or any pharmaceutical activity they might possess.

According to a process described in Gaz. Chim. Italiana 111, 257 (1981) racemic trans 1-ethyl-1-hydroxymethyl-1,2,3,4,5,6,7,12,12b-octahydroindolo[2,3-a]quinolizine was prepared by heating 1-ethyl-hexahydroindolo[2,3-a]quinolizinium perchlorate and an aqueous formaldehyde solution in acetonitrile, in the presence of diisopropyl ethyl amine. This article, too, relates to a racemic compound. There is no disclosure as to the corresponding optically active derivatives, the resolution of the compound prepared or any pharmaceutical activity of said compound or its derivatives.

We have surprisingly found that the optically active, trans (−)-1$\beta$-ethyl-1$\alpha$-hydroxymethyl-1,2,3,4,6,7,12,12b$\alpha$-octahydroindolo[2,3-a]quinolizine of the formula (I), which is not specifically disclosed in the prior art and has never been prepared before, has an excellent selective peripheral vasodilating activity, in contrast to the respective racemic compound, which shows a non-selective, general vasodilating activity. A further substantial difference is that the optically active compound according to the invention exerts its selective peripheral vasidilating activity at very low doses (e.g. a 0.03 mg./kg. i.v. dose), while the corresponding racemic compound is active in about two orders of magnitude higher doses (e.g. a 1 mg./kg. i.v. dose). A further, unexpected advantage of the compound according to the invention is its additional antihypoxial activity, which in combination with the selective peripheral vasodilating activity, provides new possibilities in therapy. The corresponding racemic compound has no antihypoxial activity at all.

The racemic compounds of the formulae (IIa) and (IIb) used as starting materials in the process according to the invention, are prepared by the process disclosed in the Hungarian Patent Specification No. 170,495 (British Patent Specification No. 1,499,546).

The resolution of the compounds of the formulae (IIa) and (IIb) may be carried out in a manner known per se. According to a preferred embodiment, for instance, the resolution is performed with an optically active acid, preferably D-tartaric acid, dibenzoyl-D-tartaric acid, camphene-sulfonic acid, etc.

Resolution is generally accomplished in an appropriately selected inert organic solvent, such as an aliphatic ketone, e.g. acetone, aliphatic alcohol or in an aqueous mixture of such solvents.

The acid addition salt formed with the optically active acid is separated into the respective diastereomeric salt pairs, and if desired, from the salt of the laevorotatory, trans compound of the formula (III) the respective base is deliberated. The deliberation of the base is preferably carried out by dissolving or suspending the salt in water or in a mixture of water and a water-immiscible organic solvent, such as an optionally halogenated aliphatic or aromatic hydrocarbon, linear or cyclic ether, e.g. dichloromethane, chloroform, ether, toluene, etc.; rendering the solution or suspension obtained alkaline with an inorganic base, such as an alkali metal carbonate, e.g. potassium or sodium carbonate, ammonia, etc.; and if desired, extracting the laevorotatory trans base of the formula (III) with any of the above-mentioned, water-immiscible organic solvents. The laevorotatory trans base of the formula (III) may, for example, be isolated from its solution in the water-immiscible organic solvent by evaporation. If desired, the crude new trans compound of the formula (III) obtained is further purified by recrystallization from a suitable solvent, such as an aliphatic alcohol having from 1 to 6 carbon atoms, e.g. methanol.

The hydrolysis of the laevorotatory trans compounds of the formula (III) is preferably carried out in an alkaline medium. Suitable bases include alkali metal alcoholates, e.g. sodium methylate, etc. Hydrolysis is preferably performed in an inert organic solvent, more preferably in an aliphatic alcohol having from 1 to 6 carbon atoms, e.g. methanol. Alternatively, the hydrolysis may be carried out with an inorganic base in an aqueous/alcoholic medium. The hydrolysis temperature generally is between 60° C. and 100° C., and preferably the reaction mixture is boiled in the inert organic solvent employed. The hydrolysis is complete within a short period of time.

The compound of formula (I), prepared according to the above-described process may, if desired, be converted into its acid addition salts by reaction with an acid according to methods known per se. Such acids include, amongst others, inorganic acids such as, for example hydrohalic acids (e.g. hydrochloric acid and hydrobromic acid), sulfuric acid, phosphoric acid and perhalic acids, e.g. perchloric acid, etc.; organic carboxylic acids such as, for example formic acid, acetic acid, propionic acid, glycolic acid, maleic acid, hydroxymaleic acid, fumaric acid, succinic acid, tartaric acid, ascorbic acid, citric acid, malic acid, salicylic acid, lactic acid, cinnamic acid, benzoic acid, phenylacetic acid, p-aminobenzoic acid, p-hydroxybenzoic acid, p-aminosalicylic acid, etc.; alkylsulfonic acids, such as, for example methanesulfonic acid, ethanesulfonic acid, etc.; cycloaliphatic sulfonic acids such as cyclohexylsulfonic acid, naphthylsulfonic acid, sulfanylic acid, etc.; amino acids, e.g. asparginic acid, glutamic acid, N-acetyl-asparaginic acid, N-acetyl-glutaric acid, etc.

Salt formation can be carried out, for example, in an inert organic solvent such as an aliphatic alcohol having from 1 to 6 carbon atoms, so that the compound of the formula (I) is dissolved in the solvent and the selected acid or a solution thereof formed with the same solvent is added to the first solution until it becomes slightly acidic (pH: 5–6). Thereafter the acid addition salt separates out and may be removed from the reaction mixture e.g. by filtration.

The compound according to the invention can, if desired, be subjected to further purification, e.g. recrystallization.

The vasodilating activity of the compound of the formula (I) was tested on anaesthesized dogs. On the femoral artery and on the internal carotis artery of the animals electromagnetic flow meter gauges (Hellige) were placed, and the blood quantity flowing in the vascular bed was determined in ml./min. The arterial mean pressure was measured by means of a Statham pressure sensor, attached to a polyethylene canulla introduced into the artery. The pulse number per minute was determined from the pulsateric component of blood pressure with a frequency meter. All measured parameters were continuously registered on a multichannel polygraph.

For comparison, in addition to the new compound according to the invention [compound of formula (I)] also the respective dextrorotatory trans compound and the known corresponding racemic trans compound were tested.

The new laevorotatory trans compound according to the invention had no effect on the pulse number and the carotis blood flow in the applied dose. All three compounds had a transitional, slight hypotensive activity. The reduction in blood pressure was about 20% in case of the known racemic compound, 6% for the (+)-isomer and 7 to 10% for the (−) isomer according to the invention. It was found that the new laevorotatory trans compound according to the invention is exceptionally active in the increase of the blood pressure in the femoral artery. For comparison also the structurally different pentoxyfilline, a widely used peripheral vasodilator, was tested. The results obtained are shown in Table 1.

Each compound was tested on more animals. The individual responses were averaged. In the tables the number of animals (n), the mean values of the measured parameters and the percentage changes are indicated.

In case of intravenous (i.v.) administration the starting basic value and the maximum change were evaluated.

TABLE 1

The effect of the test compounds on the blood flow in the femoral artery in case of i.v. administration

| compound | dose (mg./kg.) | n | blood flow (ml./min.) basic | blood flow (ml./min.) max. change | % | duration activity (min.) |
|---|---|---|---|---|---|---|
| racemic | 1.0 | 5 | 60 | 146.6 | +144 | 15.6 |
|  | 0.03 | 2 | 60 | 75 | +25 | 1 |
| (+) | 1.0 | 4 | 42.5 | 54.5 | +28 | 3.7 |
|  | 0.03 | 2 | 62 | 62 | 0 | 0 |
| (−) | 0.01 | 6 | 40.2 | 63 | +57 | 2.3 |
|  | 0.03 | 7 | 42.3 | 99.6 | +135 | 9.6 |
| pentoxy-filline | 2.0 | 5 | 49.6 | 60.6 | +22 | 1.5 |

The results set forth in Table 1 show that the peripheral vasodilating activity of the new trans (−)-stereoisomer according to the invention is superior to that of pentoxyfilline. Moreover, from the comparison with the respective racemic compound and the (+)-isomer it can be seen that the (−)-stereoisomer according to the invention is unexpectedly an about 100-times more potent peripheral vasodilator than the respective (+)-stereoisomer and about 30-times more active than the corresponding racemic compound.

Though in extreme cases it may happen that one of two possible stereoisomers essentially has the same activity as the corresponding racemic compound and accordingly, the other isomer is totally ineffective, i.e. entirely one of the two stereoisomers is responsible for the activity, this is not the case in the present invention. Our tests have led to the entirely unexpected result that the peripheral vasodilating activity of the laevorotatory trans stereoisomer according to the invention is about 30-times higher than that of the corresponding racemic compound.

Furtheron, on the basis of the results shown in Table 1 it is remarkable that while both the known racemic trans compound and the new destrorotatory trans compound are most effective at a dose of 1.0 mg/kg., the most effective dose of the new laevorotatory trans compound according to the invention is only 0.03 mg./kg. According to the data disclosed in the Table the corresponding destrorotatory trans stereoisomer was entirely ineffective, and the known racemic trans compound proved to be about 6-times less potent than the (−)-compound according to the invention when administered at this small (0.03 mg./kg.) dose. Moreover, even this low activity of the racemic compound lasts for one minute only, while the duration of the activity of the (−) trans compound according to the invention is about 10-times longer, i.e. about 10 minutes.

The antihypoxial activity of the new laevorotatory trans compound according to the invention was tested on alert mice in normobaric hypoxia. Five male mice were placed into a 3-lit. glass cylinder, which was continuously flushed with a gas mixture consisting of 96% of nitrogen and 4% of oxygen. The time passed between placing of the animals into the glass cylinder and their death was measured for each animal for a maximum period of 15 minutes. The animals which were alive at double of the average death time of the untreated animals (6.2 minutes), i.e. which were alive 12.4 minutes after the start of the experiment, were considered protected. The reference materials were administered to 20 animals each intraperitoneally, in a dose of 50 mg./kg. of body weight 30 minutes before placing the animals into the glass cylinder, while the dose of the (−) trans isomer of the formula (I) according to the invention was 25 mg./kg. The times passed until the death of the animals were averaged, and the percentage difference related to the average control time obtained with the untreated animals was calculated and called the change of the survival time (see Table 2). The number of the protected animals, i.e. the number of the animals which were still alive 12.4 minutes after their placing into the hypoxial medium, as the most important parameter characteristic of the activity, is also indicated in the Table.

The antihypoxial activity of the new laevorotatory trans compound according to the invention on the one hand was compared to the activity of the respective racemic trans compound and the corresponding dextrorotatory trans stereoisomer, on the other hand comparative studies were carried out with other racemic trans compounds disclosed in the British Patent Specification No. 1,499,546. The purpose of the latter comparative tests was to determine, whether it applies also to the other, structurally closely related compounds that the laevorotatory trans isomer has a remarkably higher and qualitatively different activity compared to the corresponding destrorotatory and racemic trans compound, respectively. The results of this test are also shown in Table 2.

TABLE 2

The effect of the test compounds on the survival time and protection of mice in hypoxial medium

| Compound | change of the average survival time related to the control (%) | Percentage of the protected animals (%) |
|---|---|---|
| known (±)-1-hydroxy-methyl derivative of formula (II) [British Pat. Spec. No. 1,499,546, (II)* R¹] | +25 | 10 |
| new (+)-1-hydroxy-methyl derivative | +15 | 10 |
| new (−)-1-hydroxy-methyl derivative [formula (I)]** | +75 | 70 |
| known (±)-1-acetoxy-methyl derivative of formula (II) [British Pat. Spec. No. 1,499,546] | +4 | 5 |
| new (+)-1-acetoxymethyl derivative | +3 | 0 |
| new (−)-1-acetoxymethyl derivative of formula (III) | +31 | 10 |
| known (±)-1-propionyloxy-methyl derivative | −11 | 0 |

TABLE 2-continued

The effect of the test compounds on the survival time and protection of mice in hypoxial medium

| Compound | change of the average survival time related to the control (%) | Percentage of the protected animals (%) |
| --- | --- | --- |
| of formula (II) [British Pat. Spec. No. 1,499,546] | | |
| new (+)-1-propionyloxymethyl derivative | +38 | 20 |
| new (−)-1-propionyloxymethyl derivative of formula (III) | −6 | 0 |

*The term "formula (II)" is used to refer to a 1:1 mixture of the compounds of formulae (IIa) und (IIb)
**25-mg./kg. dose The results set forth in Table 2 show that the new (−) trans stereoisomer according to the invention has a significant antihypoxial activity, i.e. substantially improves the hypoxia tolerance of the body tissues and organs even in small doses. The corresponding (+) trans isomer and the respective racemic trans compound are practically devoid of this activity. The antihypoxial activity is very advantageous with respect to the therapeutical indication, since in diseases accompanied by vasoconstriction the blood supply in the tissues and organs is substantially reduced, hypoxia takes place which results in tissue necrosis. Therefore, the combination of the vasodilating effect with the increase of cell resistance against hypoxia is very favorable therapeutically.

The known racemic and the dextrorotatory trans compounds have no antihypoxial activity even in higher doses. The 10% frequency of protection is namely not significant statistically, since also the untreated animals may prove protected in about the same ratio.

It can further be seen that out of the tested, structurally closely related compounds solely the new laevorotatory trans isomer according to the invention possesses this significant and new activity when compared to the corresponding racemic and dextrorotatory trans compounds. Neither the racemic trans 1-acetoxymethyl nor 1-propionyloxymethyl derivatives disclosed in the British Patent Specification 1,499,546 nor the respective new optically active laevorotatory compounds of the formula (III) obtained by the resolution of the former compounds, or the corresponding dextrorotatory compounds have any significant antihypoxial activity.

The new laevorotatory trans compound of the formula (I) may be used advantageously in the therapy, first of all in the treatment of diseases accompanied by vasoconstriction. The expected therapeutical dose is 0.01 to 1.0 mg./kg. of body weight in case of parenteral administration and 0.5 to 5.0 mg./kg. of body weight in case or oral administration.

The new compound of the formula (I) and its physiologically acceptable salts may be formulated for therapeutic purposes. The invention therefore relates also to pharmaceutical compositions comprising as active ingredient the compound of formula (I) or a physiologically acceptable acid addition salt thereof, in association with pharmaceutical carriers and/or excipients. Carriers conventional for this purpose and suitable for parenteral administration as well as other additives may be used. As carriers solid or liquid compounds, for example water, gelatine, lactose, starch, pectin, magnesium stearate, stearic acid, talc, vegetable oils such as peanut oil, olive oil, etc. can be used. The compounds can be formulated as conventional pharmaceutical formulations, for example in a solid (globular and angular pills, dragées, capsules, e.g. hard gelatine capsules) or liquid (injectable oily or aqueous solutions or suspensions) form. The quantity of the solid carrier can be varied within wide ranges, but preferably is between 25 mg. and 1 g. The compositions optionally contain also conventional pharmaceutical additives, such as preserving agents, wetting agents, salts for adjusting the osmotic pressure, buffers, flavoring and aroma substances.

The compositions according to the invention optionally contain the compound of the formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatment, such as sterilization.

The invention is elucidated in detail by the aid of the following non-limiting Examples.

EXAMPLE 1

(+)-1β-Acetyloxymethyl-1α-ethyl-1,2,3,4,6,7,12,12bβ-octahydroindolo[2,3-a]quinolizine and
(−)-1α-acetyloxymethyl-1β-ethyl-1,2,3,4,6,7,12,12bα-octahydroindolo[2,3-a]quinolizine A solution of 1.1319 g (7.54 mmoles) of D-tartaric acid in 25 ml. of absolute acetone is added to a hot solution of 1.3619 g. (7.54 mmoles) of (+)-1-acetyloxymethyl-1-ethyl-1,2,3,4,6,7,12,12b-octahydroindolo[2,3-a]quinolizine (British Patent Specification No. 1,499,546) in 25 ml. of absolute acetone. The mixture is allowed to stand at room temperature for 24 to 28 hours. The precipitated crystals are filtered off and after washing with a minimum amount of acetone 2.00 g. of the corresponding tartarate are obtained. The salt is dissolved in 50 ml. of distilled water, and the solution is adjusted to pH 8 with a 5% aqueous sodium carbonate solution under cooling with ice water. The alkaline solution is extracted with three 20-ml. portions of dichloromethane. The combined organic solution is dried over solid anhydrous magnesium sulfate and is then evaporated in vacuum. The residual oil is crystallized from methanol. 1.20 g. (97.4%) of the dextrorotatory title compound are obtained as a crystalline substance.

Melting point: 122° C. to 123° C.

$[\alpha]_D = +38.7°$ (c=1, dichloromethane).

Evaporation of the mother liquor of resolution in vacuum affords 1.65 g. of a solid foam. Essentially following the above-described procedure and crystallizing the product from methanol 1.00 g. (81.2%) of the laevorotatory title compound is obtained.

Melting point: 122° C. to 123° C.

$[\alpha]_D = -37.5°$ (c=1, dichloromethane).

EXAMPLE 2

(+)-1α-Ethyl-1β-hydroxymethyl-1,2,3,4,6,7,12,12bβ-octahydroindolo[2,3-a]quinolizine and
(−)-1β-ethyl-1α-hydroxymethyl-1,2,3,4,6,7,12,12-bα-octahydroindolo[2,3-a]quinolizine (a) 1.95 g. (5.97 mmoles) of the (+)-1β-acetyloxymethyl-1α-ethyl-1,2,3,4,6,7,12,12bβ-octahydroindolo[2,3-a]quinolizine prepared according to Example 1 are dissolved in 100 ml. of hot methanol and following the addition of 0.05 g. (0.92 mmole) of sodium methylate the mixture is refluxed for 30 minutes. The reaction mixture is allowed to cool to room temperature, then poured onto 300 ml. of distilled water and the precipitated white crystals are filtered off and washed with cold water.

1.65 g. (97.6%) of the dextrorotatory title compound are obtained as a white, crystalline substance.

Melting point: 220° C. to 221° C.

$[\alpha]_D = +110.04°$ (c=1, dimethyl formamide).

(b) Essentially following the procedure described under point (a) but starting from (−)-1α-acetyloxymethyl-1β-ethyl-1,2,3,4,6,7,12,12bα-octahydroindolo[2,3-a]quinolizine prepared according to Example 1 1.60 g. (94.2%) of the laevorotatory title compound are obtained as a crystalline substance.

Melting point: 220° C. to 221° C.

$[\alpha]_D = -108.0°$ (c=1, dimethyl formamide).

The hydrogen bromide of the laevorotatory title compound is prepared from a 10-fold volume of hot acetone with a 48% aqueous hydrogen bromide solution.

Melting point: 280° C. to 282° C.

Melting point after crystallization from methanol: 285° C. to 287° C.

We claim:

1. (−)-1β-Ethyl-1α-hydroxymethyl-1,2,3,4,6,7,12,12bα-octahydroindolo[2,3-a]quinolizine of the formula (I)

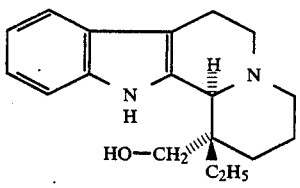

(I)

and pharmaceutically acceptable acid addition salts thereof.

2. Pharmaceutical composition having peripheral vasodilating and antihypoxic activity comprising as active ingredient a therapeutically effective amount of the compound of formula (I) as defined in claim 1 or a physiologically acceptable acid addition salt thereof, in association with an inert pharmaceutical carrier or excipient.

3. A method of treating a mammalian subject to effect peripheral vasodilation which comprises the step of orally administering to said mammalian subject 0.5 to 5.0 mg/kg of body weight of the compound of the Formula (I)

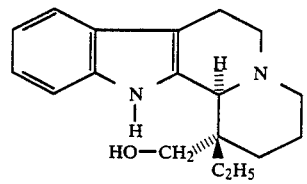

or a pharmaceutically acceptable acid addition salt thereof.

4. A method of treating a mammalian subject suffering from vasoconstriction to effect an antihypoxic effect which comprises the step of orally administering to said mammalian subject a therapeutically effective amount of a compound of the Formula (I)

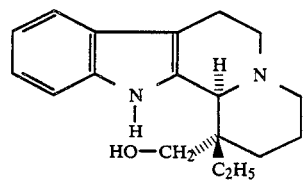

or a pharmaceutically acceptable acid addition salt thereof.

5. A method of treating a mammalian subject to effect peripheral vasodilation which comprises the step of parenterally administering to said mammalian subject 0.01 to 0.03 mg/kg of body weight of the compound of the Formula (I)

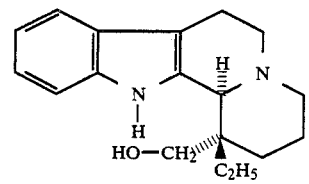

or a pharmaceutically acceptable acid addition salt thereof.

6. A method of treating a mammalian subject suffering from vasoconstriction to effect an antihypoxic effect which comprises the step of parenterally administering to said mammalian subject a therapeutically effective amount of the compound of the Formula (I)

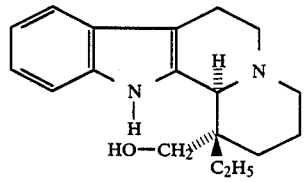

or a pharmaceutically acceptable acid addition salt thereof.

7. A method of treating a mammalian subject defined in claim 6 wherein the compound of the Formula (I) is intraperitoneally administered to a mammalian subject in an amount of about 25 mg/kg of body weight.

* * * * *